US005681969A

United States Patent [19]

Nolen et al.

[11] Patent Number: 5,681,969
[45] Date of Patent: Oct. 28, 1997

[54] CONTINUOUS PROCESS FOR THE CONVERSION OF 2,5-DIHYDROFURAN TO 2,3-DIHYDROFURAN

[75] Inventors: Timothy Richard Nolen; Stephen Neal Falling; David Martin Hitch; Jerry Lynn Miller; Daniel Latham Terrill, all of Kingsport, Tenn.

[73] Assignee: Eastman Chemical Company, Kingsport, Tenn.

[21] Appl. No.: 642,544

[22] Filed: May 3, 1996

[51] Int. Cl.$^6$ .................................. C07D 315/00
[52] U.S. Cl. ................................................ 549/507
[58] Field of Search ................................ 549/507

[56] References Cited

U.S. PATENT DOCUMENTS

| | | | |
|---|---|---|---|
| 2,556,325 | 6/1951 | Fluchaire et al. | 260/345 |
| 5,082,956 | 1/1992 | Monnier et al. | 549/507 |
| 5,117,012 | 5/1992 | Stavinoha et al. | 549/538 |
| 5,254,701 | 10/1993 | Falling et al. | 549/475 |
| 5,312,931 | 5/1994 | Stavinoha | 549/538 |
| 5,315,019 | 5/1994 | Phillips et al. | 549/507 |
| 5,362,890 | 11/1994 | Stavinoha et al. | 549/536 |
| 5,536,851 | 7/1996 | Monnier | 549/507 |

FOREIGN PATENT DOCUMENTS 1248669  1/1965  Germany.

*Primary Examiner*—Amelia Owens
*Attorney, Agent, or Firm*—J. Frederick Thomsen; Harry J. Gwinnell

[57] ABSTRACT

Disclosed is a process for the continuous production and recovery of 2,3-dihydrofuran (2,3-DHF) by the isomerization of 2,5-dihydrofuran (2,5-DHF) which contains certain impurities to 2,3-dihydrofuran in yields exceeding 95%. The process utilizes, in order, an isomerization zone containing one or more beds of a supported, palladium or platinum catalyst, a product recovery zone comprising a distillation column, a high boiler removal zone and means for feeding the 2,5-DHF component of the bottoms stream from the product recovery zone to the isomerization zone.

6 Claims, 1 Drawing Sheet

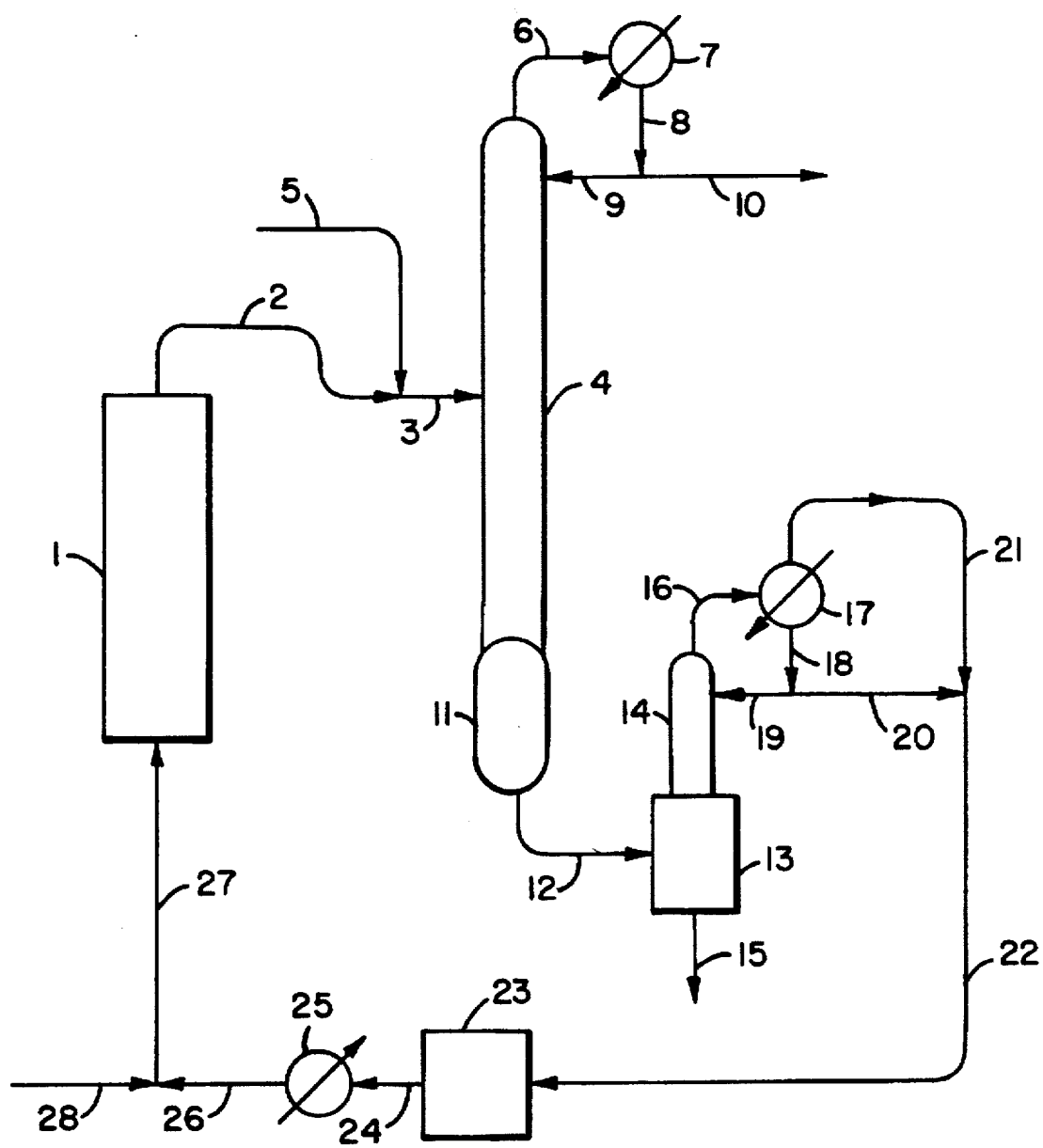
Figure

CONTINUOUS PROCESS FOR THE CONVERSION OF 2,5-DIHYDROFURAN TO 2,3-DIHYDROFURAN

This invention pertains to a process for the continuous production and recovery of 2,3-dihydrofuran (2,3-DHF) from 2,5-dihydrofuran (2,5-DHF). More specifically, this invention pertains to a process for Converting 2,5-dihydrofuran which contains certain impurities to 2,3-dihydrofuran in yields exceeding 95%.

The isomerization of 2,5-DHF to 2,3-DHF is a step in the synthesis of two important chemicals, 1,4-butanediol and cyclopropanecarboxaldehyde. It is known (U.S. Pat. No. 2,556,325) that 2,5-DHF may be isomerized to 2,3-DHF in the presence of alkali metal alkoxide. Another method for accomplishing this isomerization (U.S. Pat. No. 5,254,701) utilizes a ruthenium- or rhodium-based catalyst in a homogeneous, liquid-phase system. However, the ruthenium- and rhodium-based catalysts are highly susceptible to poisoning by low level impurities, e.g., 3,4-epoxy-1-butene, crotonaldehyde, oxygen and peroxides, often found in the 2,5-DHF feedstock.

German Patent 1,248,669 discloses the hetero-geneous, catalytic isomerization of 2,5-DHF to 2,3-DHF using certain metal catalysts such as palladium, platinum, cobalt, ruthenium and nickel. However, the selectivity of the process of German Patent 1,248,669 for converting 2,5-DHF to 2,3-DHF is only in the range of 75–85%. Early efforts to conduct the heterogeneous, palladium- or platinum-catalyzed reaction utilizing gaseous 2,5-DHF resulted in considerable formation of the undesired disproportionation byproducts furan and tetrahydrofuran. It has been discovered previously that the selectivity of the heterogeneous, palladium- and platinum-catalyzed isomerization of 2,5-DHF to 2,3-DHF can be increased by including carbon monoxide (CO), or a compound which generates carbon monoxide under the isomerization conditions, in the gaseous feed of 2,5-DHF.

It also has been found that contacting a gas mixture of 2,5-DHF, nitrogen and CO with a supported palladium catalyst gave a selectivity to 2,3-DHF of about 90% or less when the isomerization reaction is operated at or near 100% conversion. However, selectivities of above 97% can be obtained by operating the isomerization reaction at approximately 50% conversion per pass through the isomerization reactor. As used herein, "percent conversion of 2,5-DHF" means:

$$\frac{\text{Moles 2,5-DHF converted to products}}{\text{Moles 2,5-DHF fed}} \times 100$$

and "percent selectivity to 2,3-DHF" means:

$$\frac{\text{Moles 2,5-DHF converted to 2,3-DHF}}{\text{Moles 2,5-DHF converted to total products}} \times 100$$

The nonselective products are formed primarily by the disproportionation of DHF to furan and tetrahydrofuran.

Therefore, in an attempt to obtain high overall yields and selectivity to 2,3-DHF, a production system was designed whereby only a portion of the 2,5-DHF fed to the isomerization zone was converted to products and unreacted 2,5-DHF was recovered and recycled to the isomerization zone. The production system comprised an isomerization zone, a product recovery zone, a high boiler removal zone and means for recycling the 2,5-DHF recovered in the product recovery zone along with fresh 2,5-DHF to the isomerization zone. The process initially involved feeding a gaseous mixture comprising fresh and recycled 2,5-DHF, a nonreactive gas such as nitrogen and CO to the isomerization zone where it contacted a supported palladium or platinum catalyst. The effluent from the isomerization zone was fed to the product recovery zone comprising a distillation column which produced a product stream comprising 2,3-DHF overhead and a liquid bottoms stream comprising 2,5-DHF from the base of the column. The bottoms stream was fed to a high boiler removal zone comprising distillation apparatus for the removal of high boilers formed in the isomerization and the product recovery zones. The removal of high boilers is necessary since they cause a reduction in the activity of the isomerization catalyst. The high boiler removal zone produced a minor stream comprising high boilers and a major stream comprising 2,5-DHF which was recycled to the isomerization zone with fresh 2,5-DHF. Operation of the production system initially designed resulted in catalyst deactivation which was found to be due, at least in part, to the high boilers present in the fresh 2,5-DHF feedstock.

The initial process design then was modified by feeding the fresh 2,5-DHF feedstock to the high boiler removal zone to remove the high boilers present in the feedstock. When the modified process was operated continuously, rapid deactivation of the isomerization catalyst again was observed. An examination of the deactivated catalyst indicated that inactivation was related to iodine. It was then discovered that the fresh 2,5-DHF feedstock contained methyl iodide in a concentration of less than 1 part per million (ppm). Methyl iodide is a low boiling compound (b.p. 46° C.) compared to both 2,5-DHF (b.p. 66° C.) and 2,3-DHF (b.p. 55° C.) and therefore is not removed in the high boiler removal column. The presence of iodine was observed previously in the high boiler liquid produced by the high boiler removal column. It was assumed that all of the iodine resulted from high boiler iodine compounds derived from the catalyst used to produce the 2,5-DHF feedstock. As high boiling species, these iodine compounds should have been sufficiently removed from the fresh 2,5-DHF which, as noted above, was fed to the high boiler removal zone which comprises a packed column on top of a vaporizer. Gas chromatography (GC) analysis of the feed to, and the vapor effluent from, the high boiler removal zone showed that the column was very effective in removing high boilers. The presence of methyl iodide in the 2,5-DHF was totally unexpected.

The 2,3-DHF production process was again modified to change the fresh 2,5-DHF feed point to the product recovery column of the above described production system. The methyl iodide contained in the 2,5-DHF feedstock is removed from the production system with the 2,3-DHF product obtained from the product recovery zone. The process as modified can be operated over prolonged periods of time without any significant deactivation of the isomerization catalyst. The present invention, therefore, provides a system for the continuous production of 2,3-DHF by the isomerization of 2,5-DHF comprising an isomerization zone containing one or more beds of a supported, palladium or platinum catalyst, a product recovery zone comprising a distillation column, a high boiler removal zone and means for feeding 2,5-DHF obtained from the high boiler removal zone to the isomerization zone, comprising the steps of:

(1) feeding the product of step (3) and fresh 2,5-DHF to the distillation column of the product recovery zone to obtain (i) an overhead vapor stream rich in 2,3-DHF from the top or upper section of the column and (ii) a bottoms liquid stream (column underflow) rich in 2,5-DHF from the base or lower section the column;

(2) feeding liquid from step (1)(ii) to a high boiler removal zone comprising distillation means to obtain (i) a liquid bottoms stream comprising high boilers and
(ii) a distillate stream comprising 2,5-DHF; and
(3) feeding a vapor comprising 2,5-DHF from step (2)(ii) to the isomerization zone to produce an isomerization product comprising 2,3-DHF and 2,5-DHF.

The concentration of the methyl iodide in the 2,3-DHF product is too low to affect downstream processes but is sufficiently high to have an adverse affect on the isomerization catalyst used in the process of the invention.

The accompanying FIGURE is a process flow diagram illustrating a 2,3-DHF production system embodying the principles of the processes of the present invention. While the present invention is susceptible to embodiment in various forms, there is shown in the FIGURE and hereinafter described in detail preferred embodiments of the invention. However, the present disclosure is to be considered as an exemplification of the invention without limitation to the specific embodiments illustrated.

The 2,5-DHF used in the present process may be obtained from 1,3-butadiene by the steps of (1) partially oxidizing butadiene to 3,4-epoxy-1-butene and (2) isomerizing the 3,4-epoxy-1-butene to 2,5-DHF. The selective oxidation of butadiene to 3,4-epoxy-1-butene may be accomplished by the processes described in U.S. Pat. Nos. 5,117,012, 5,312,931 and 5,362,890. The isomerization of 3,4-epoxy-1-butene to 2,5-DHF may be carried out by the processes disclosed in U.S. Pat. Nos. 5,082,956 and 5,315,019.

The fresh 2,5-DHF used in the process of the present invention typically contains about 0.1 to 5 weight percent of a mixture of 3,4-epoxy-1-butene (EpB) and crotonaldehyde (HCr) and trace amounts of other high boilers and low boilers including low boiling iodide compounds such as methyl iodide. The concentration of the low boiling iodide compound(s) in the fresh 2,5-DHF feed may be in the range of about 0.01 to 100 ppm with a concentration of about 0.1 to 5 ppm being more typical. Essentially all of the low boilers (compounds boiling at or below 55° C.), e.g., methyl iodide, contained in the fresh 2,5-DHF are removed from the production system in the overhead vapor stream obtained from the distillation column of the product recovery zone. The high boilers present in trace amounts in the 2,5-DHF feedstock are believed to be phosphorus- and tin-containing components of the catalyst system (or decomposition products thereof), and oligomers, diols and iodobutenols derived from the 3,4-epoxy-1-butene, used in the manufacture of the 2,5-DHF feedstock. During the operation of the isomerization process, the 3,4-epoxy-1-butene present in the feedstock is rapidly and quantitatively isomerized to crotonaldehyde; the crotonaldehyde is partially decarbonylated to CO and propene and partially hydrogenated to butyraldehyde; and the butyraldehyde is partially decarbonylated to CO and propane.

The distillation used to separate 2,3-DHF from 2,5-DHF in the product recovery zone is a conventional distillation operation. The distillation column typically includes at least two sections, each containing either packing or distillation trays. The column typically has a condenser to condense the overhead vapor, some of which is taken as the distillate product and the rest of which is refluxed to the column to provide liquid flow on the packing or trays. Vapor in the column is generated by a heat source, e.g. a reboiler, at the base of the column that boils some of the liquid reaching the bottom of the column while the remainder, containing mostly 2,5-DHF, is drained from the reboiler and fed to the high boiler removal zone and ultimately fed to the isomerization zone. The temperature profile of the column, when operated at approximately atmospheric pressure, typically is about 63° to 68° C. at the column base, about 55° to 58° C. at the midpoint of the column and about 53° to 56° C. near the top of the column. The product from the isomerization zone and the fresh 2,5-DHF may be fed separately to the distillation column at one or more points at the lower, middle and/or upper sections of the column. Typically, the product of the isomerization zone and the fresh 2,5-DHF are fed separately or as a combined stream to the mid-section of the distillation column. The weight ratio of the product of the isomerization zone fed to the column to the fresh 2,5-DHF fed to the column is in the range of about 4:1 to 1:4, preferably about 3:2 to 2:3. The feeds preferably are fed as liquids so that the required column diameter needed is minimized. The amount of liquid refluxed at the top of the column and the number of theoretical plates of separation needed depends on the purity of product desired. Typically, between 20 and 100 plates would be used with a reflux:distillate-product ratio of 5:1 to 25:1.

The overhead vapor product from the product recovery zone is one of only two outlets for the production system. The other outlet is the liquid obtained from the high boiler removal zone. Essentially all of the furan (b.p. 31° C.) is taken overhead with the 2,3-DHF product. Some 2,5-DHF (b.p. 66° C.) normally is allowed to go overhead so that a small amount of tetrahydrofuran (b.p. 66° C.) is removed from the production system in the 2,3-DHF product. Some 2,3-DHF normally is taken out in the bottoms liquid and recycled to the isomerization zone. The composition (by weight) of the overhead product stream is about 90 to 97% 2,3-DHF, about 0.5 to 5% 2,5-DHF, about 1 to 5% furan, and about 0.1 to 1% tetrahydrofuran.

The bottoms liquid stream obtained from the product recovery zone is fed to the high boiler removal zone which comprises a heated vessel fitted with a section of packed column to prevent high boilers from being fed to the isomerization zone. Approximately 0.1 to 2 weight percent of the liquid stream fed to the high boiler removal zone is removed from the production system as a high boiler (liquid bottoms) stream. The high boilers removed comprise primarily compounds having a boiling point above about 120° C. The distillation means of the high boiler removal zone, when operated at approximately atmospheric pressure, typically is operated at a temperature in the range of about 65° to 80° C. Normally, a portion of the distillate vapor is condensed and returned to the packed column as reflux. Alternatively, the entire distillate stream may be condensed with part of the liquid being returned to the packed column of the high boiler removal zone and the remainder being fed to the isomerization zone.

In addition to the high boilers (mentioned above) contained in the fresh 2,5-DHF feedstock, the feed to the high boiler removal zone also includes intermediate boiling compounds produced in the isomerization and/or product recovery zones. Such intermediate boiling compounds include tetrahydrofuran (THF, b.p. 66° C.), butyraldehyde (HBu, b.p. 75° C.), crotonaldehyde (HCr, b.p. 104° C.), 1-butanol (BuOH, b.p. 118° C.), 2-buten-1-ol (b.p. 121° C.), and methyl ethyl ketone (MEK, b.p. 80° C.), and DHF dimers. A weak base such as a tertiary amine, e.g., triethanolamine, may be fed to the heated vessel (vaporizer) to inhibit polymerization of the 2,3-DHF in the high boiler removal zone. A phenolic antioxidant such hydroquinone, butylated hydroxyanisole, butylated hydroxytoluene (BHT) and the like also may be added to the heated vessel to prevent or scavenge peroxides which may collect in the vessel.

All or a portion of the distillate stream obtained from the high boiler removal zone is transferred and fed to the isomerization zone. The means employed to accomplish the transfer may permit condensation of distillate vapor and collection of the condensed liquid in an isomerization zone feed tank. The liquid feed material then is vaporized prior to entering the isomerization zone. Alternatively, distillate vapor from the high boiler removal zone may be fed directly to the isomerization zone without condensation. The distillate stream obtained from the high boiler removal zone typically comprises, by weight, about 1 to 20% tetrahydrofuran, about 1 to 10% 2,3-DHF, a total of about 1 to 10% of 3,4-epoxy-1-butene, crotonaldehyde, butyraldehyde and methyl ethyl ketone, and about 65 to 95% 2,5-DHF.

The supported catalysts useful in the isomerization zone of the present invention comprise palladium, platinum, or a mixture thereof, in the form of metals, deposited on a catalyst support material. The amount of the palladium and/or platinum metal component of the catalysts may be in the range of 0.1 to 10 weight percent with amounts of 0.2 to 5.0 weight percent being preferred. Supported catalysts comprising 0.5 to 3.0 weight percent palladium are particularly preferred.

The support material component of the catalysts may be selected from the large number of nonacidic, conventional, porous, carbon or refractory catalyst carriers or support materials which are essentially inert in the presence of the reactant, product, diluent and carbon monoxide present in the processes in which the catalysts are employed. Such conventional materials may be of natural or synthetic origin and preferably are of a mesoporous or macroporous structure, i.e., support materials having a surface area below 100 square meters per gram ($m^2/g$). These support materials typically have an apparent porosity of greater than 20%. Supports having a siliceous and/or aluminous composition are, in general, preferred.

Specific examples of suitable supports are activated carbon, the aluminum oxides (including the materials sold under the trade name "Alundum"), pumice, magnesia, zirconia, kieselguhr, fuller's earth, silicon carbide, porous agglomerates comprising silicon and/or silicon carbide, silica, selected clays, artificial and natural zeolites and ceramics. Refractory supports particularly useful in the preparation of the catalysts useful in the process of our invention comprise siliceous and/or aluminous materials, and in the case of aluminous materials, particularly those containing alpha alumina. In the case of alpha alumina-containing supports, preference is given to those having a specific surface area as measured by the B.E.T. method of from 0.03 to 10 $m^2/g$ and an apparent porosity as measured by conventional mercury or water absorption techniques of from 25 to 50% by volume. The B.E.T. method for determining specific surface area is described in detail in Brunauer, S., Emmett, P. H., and Teller, E., J. Am. Chem. Soc., 60, 309–16 (1938).

The following materials are specific examples of the catalyst supports which may be used.

I. Star-shaped silica support, typically having a surface area of 20–80 $m^2/g$, a total pore volume of 0.3 to 0.7 cc(Hg)/g, median pore diameter of 100–500 microns ($\mu$), and a chemical composition composed substantially of $SiO_2$.

II. Norton SN-08228, 0.1875 inch pellets with a surface area of 0.26 $m^2/g$, a total pore volume of 0.23 cc(Hg)/gm, median pore diameter of 19$\mu$, a packing density of 0.90 $g/cm^3$, and a chemical composition (weight percent) of: alumina—84.7, $SiO_2$—13.4, $Fe_2O_3$—0.21, $TiO_2$—0.47, $CaO$—0.21, $MgO$—0.12, $Na_2O$—0.15, $K_2O$—0.26.

III. Norton SA-5252, 0.1875 inch spheres with a surface area of 0.39 $m^2/g$, a total pore volume of 0.36 cc(Hg)/gm, median pore diameter of 5.4$\mu$, a packing density of 0.94 $g/cm^3$ and a chemical composition (weight percent) as follows: $Al_2O_3$—93.1, $SiO_2$—5.6, $Fe_2O_3$—0.3, $TiO_2$—0.1, $CaO$—0.1, $MgO$—0.3, $Na_2O$—0.1, $K_2O$—0.1.

IV. Norton 5552 Alumina Rings—0.25 inch rings having a surface area of 0.43 $m^2/g$, a total pore volume of 0.37 cc (Hg)/gm, a median pore diameter of 7$\mu$, a packing density of 0.80 $g/cm^3$, and a chemical composition (weight percent) of: $Al_2O_3$—93.1, $SiO_2$—5.6, $Fe_2O_3$—0.3, $TiO_2$—0.1, $CaO$—0.1, $MgO$—0.3, $Na_2O$—0.1, $K_2O$—0.1.

V. Norton SN-82501, 0.1875 inch spheres having a surface area of 0.13 $m^2/g$, a total pore volume of 0.37 cc(Hg)/gm, a median pore diameter of 32.5$\mu$, a packing density of 0.88 $g/cm^3$, and a chemical composition (weight percent) of: $Al_2O_3$—85.0, $SiO_2$—12.0, and the remaining 3% as $Fe_2O_3$, $TiO_2$, $CaO$, $MgO$, $Na_2O$ and $K_2O$.

Although not preferred, other support materials which may be used include zinc oxide, e.g., having a surface area of 3–10 $m^2/g$ and a particle size of 75–250$\mu$; titania, e.g., having a surface area of 0.5 $m^2/g$ and a particle size of 40–75$\mu$; calcium oxide; barium oxide, e.g., having a surface area of 1 $m^2/g$ and a particle size of 40–75$\mu$; boron nitride; and silicon carbide.

A preferred class of support materials comprise extruded star-shaped silica supports which have relatively uniform pore diameters and are more fully characterized by having (1) B.E.T. specific surface areas of from 20 $m^2/g$ to 80 $m^2/g$, preferably 70 $m^2/g$, and (2) apparent porosities of from 20% to 70%, preferably from 30% to 60%.

The actual physical form of the catalyst support is not particularly important. While the form of the catalyst support has little effect on catalyst activity, practical considerations such as ease of heat transfer, mass transfer, pressure drop due to fluid flow restrictions, efficiency of gas-liquid-solid contacting, catalyst durability, and the like make the use of defined shapes such as stars, spheres, pellets, extrudates, rings, saddles, and the like preferred.

The isomerization zone may be operated under a broad range of pressure and temperature conditions. Pressure is not an important feature of the isomerization process and thus pressures moderately above or below atmospheric are used. Pressures of 0.1–50 bars absolute, preferably 1–20 bars absolute, may be used although operation at approximately atmospheric pressure is most preferred. It is apparent that vapor phase operation requires the use of pressures which, in combination with the process temperature, will cause the reactant and product to be present in the reactor as vapors. The isomerization may be carried out at temperatures in the range of 30° to 175° C., preferably in the range of 50° to 130° C., and, most preferably, in the range of 80° to 110° C. Generally, the temperatures employed with platinum catalysts are higher than those used with palladium catalysts.

The temperatures and gas hourly space velocity (GHSV) utilized in the isomerization zone are selected to give a percent conversion of about 20 to 90 mole percent of the 2,5-DHF fed with conversions in the range of 40 to 60 mole percent being particularly preferred. GHSV is the volumetric flow rate of gas (feed material plus any diluent used) fed to the isomerization zone divided by the volume of the catalyst present in the reactor.

The feed to the isomerization zone preferably includes a selectivity-increasing amount of (i) carbon monoxide, (ii) an aldehyde selected from alkanals containing 2 to 5 carbon atoms and alkenals containing 3 or 4 carbon atoms, (iii) 3,4-epoxy-1-butene, or (iv) a mixture of 2 or more of such carbon monoxide, aldehydes or 3,4-epoxy-1-butene. Examples of the aldehydes which may be used the process to provide an increase in selectivity include those having the general formula

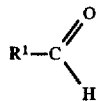

wherein $R^1$ is $C_1$–$C_4$ alkyl, vinyl or allyl. Specific examples of the aldehydes include crotonaldehyde, acetaldehyde, propionaldehyde, n-butyraldehyde, isobutyraldehyde, valeraldehydes, acrolein and vinyl acetaldehyde. These compounds may be added to the 2,5-DHF feedstream intentionally or be present in the feedstream as impurities, e.g., 1,3-butadiene may be selectively oxidized to 3,4-epoxy-1-butene which in turn can be converted to 2,5-DHF, all according to known processes, to give 2,5-DHF which may contain trace or minor amounts of crotonaldehyde and/or 3,4-epoxy-1-butene.

The amount of the above-described epoxides and/or aldehydes which may be used to exert a favorable effect on selectivity varies substantially depending upon such factors as the particular catalyst and reaction conditions, especially temperature, used. Generally, the amount of epoxide/aldehyde present in the feed to the isomerization process is in the range of 5 to 20,000 parts per million by volume (ppmv), preferably 10 to 10,000 ppmv and, most preferably, 100 to 5000 ppmv based on the total volume of the gas fed to the reactor, i.e., the volume of the 2,5-DHF reactant and any diluent gas or liquid present.

When carbon monoxide is used alone, i.e., in the absence of one of the above-described epoxides or aldehydes, the amount of the carbon monoxide which will significantly increase the selectivity of the catalyst can vary substantially depending upon factors such as the particular catalyst and reaction temperature used. Generally, the amount of carbon monoxide present during isomerization is in the range of 5 to 5,000 parts per million by volume (ppmv) based on the total volume of the gas fed to the reactor, i.e., the volume of the 2,5-DHF reactant and any diluent gas present. The carbon monoxide concentration preferably is 50 to 1500 ppmv, most preferably 50 to 750 ppmv. Atypical carbon monoxide concentration in the feed in gas phase operation is about 500 ppmv. High levels of carbon monoxide tend to give better selectivity to the desired 2,3-DHF product. However, if the selectivity is too high the rate of formation of 2,3-DHF is reduced to an unacceptable level.

Carbon monoxide usually will be used in the process of the present invention in combination with 3,4-epoxy-1-butene and/or one or more of the above-described aldehydes, particularly 3,4-epoxy-1-butene and croton-aldehyde, to enhance selectivity. For example, carbon monoxide may be added to the 2,5-DHF reactant which contains only a trace amount of such epoxide and/or aldehyde to achieve a desired combination of selectivity and conversion. Generally, the amount of carbon monoxide which optionally may be added to the feed is in the range of 5 to 5,000 ppmv based on the total volume of the gas fed to the reactor, i.e., the total volume of the 2,5-DHF reactant, 3,4-epoxy-1-butene and/or the above-described aldehydes and any diluent gas or liquid present. In gas phase operation, the carbon monoxide concentration preferably is 50 to 1500 ppmv, most preferably 50 to 750 ppmv. A typical carbon monoxide concentration in the feed in gas phase operation is 300 ppmv. As in the case of the above-described epoxides/aldehydes, the effect of carbon monoxide also is reversible and thus, the removal of both epoxide/aldehyde and carbon monoxide from the process restores the activity of the catalyst to that which existed before the epoxide/aldehyde and carbon monoxide were added.

Referring to the accompanying FIGURE, an isomerization product obtained from isomerization zone 1 is transferred by means of conduits 2 and 3 to the mid-section of distillation column 4 of the product recovery zone. Fresh 2,5-DHF is fed to conduit 3 and fed with the isomerization product to column 4. It is preferred, but not essential, that the isomerization product removed from isomerization zone 1 is allowed to condense in conduits 2 and 3 and, with the fresh 2,5-DHF feed-stock, fed as a liquid to column 4. It is apparent to those skilled in the art that the fresh 2,5-DHF feed-stock can be fed, separately to column 4 at one or more points along the side of the column. Normally, column 4 contains at least one section of trays or packing above and below to point at which the stream of conduit 3 enters the column.

The overhead effluent comprising 2,3-DHF produced by column 4 is removed from the top of the column via conduit 6, fed to condenser 7 and removed from the production system by means of conduits 8 and 10. A 5 portion of the condensed effluent is returned as reflux to the column through conduits 8 and 9. Typical reflux ratios (the ratio of the weight of condensed effluent returned to the column via conduit 9 to the weight of condensed effluent/product which is removed from the system via conduit 10) may be used in the operation of the product recovery zone are about 5:1 to 25:1. The product typically comprises about 90 to 97% 2,3-DHF, about 0.5 to 5% 2,5-DHF and about 1 to 5% of a mixture of THF and furan. The purity of the product normally is sufficient to permit its use, without further purification, in the manufacture of other products such as 2-hydroxytetrahydrofuran and cyclopropanecarboxaldehyde.

A liquid comprising 2,5-DHF collects in reboiler 11 at the base of column 4. Reboiler 11 provides the heat for the operation of column 4. A portion, e.g., about 80 to 96 weight percent, of the liquid is vaporized by reboiler 11 and returned to column 4. The remainder of the liquid collected in reboiler 11 is transported via conduit 12 to vaporizer 13 which, in combination with column 14, comprises the high boiler removal zone. The composition (by weight percent) of the liquid underflow from column 4 and reboiler 11 typically is about 65 to 95% 2,5-DHF, about 1 to 10% 2,3-DHF, about 1 to 20% THF and about 0.5 to 10% of a mixture comprised of EpB, HCr, HBu and/or MEK. As stated above, a weak base such as a tertiary amine, e.g., triethanolamine, may be fed to vaporizer 13 or to distillation column 4, either through an additional feedport (not shown) or via conduits 8 or 9, to inhibit polymerization of the 2,3-DHF in the high boiler removal zone. A phenolic antioxidant such hydroquinone, butylated hydroxyanisole, butylated hydroxytoluene (BHT) and the like also may be added to vaporizer 13 to control peroxides. Vaporizer 13 may be operated at a temperature of about 65° to 80° C. to cause about 98 to 99.9 weight percent of the liquid fed to the vaporizer to distill from the high boiler removal zone for recovery and transfer to isomerization zone 1. Typically, the amount of the liquid fed to vaporizer 13 which is distilled from the high boiler removal zone is about 99 to 99.7 weight percent. The high boiling residue remaining in the vaporizer is removed from the production system through conduit 15. A typical composition of the residue is (by weight percent) 2.3% 2,3-DHF, 0.1% EpB, 2.8% HBu, 1.1% MEK, 74.9% 2,5-DHF, 12.3% THF, 0.46% HCr, 0.01% butanol, 0.19% 2-buten-1-ol, 1.42% DHF dimers and 2.35% BHT.

The material distilled from the high boiler removal zone is fed via conduit 16 to condenser 17 wherein some or all of the vapor effluent from column 14 is condensed. In one mode of operation, all of the vapor effluent is condensed in condenser 17 and a portion, e.g. 20 to 80 weight percent, of the condensate is returned by means of conduits 18 and 19 to column 14 as reflux. The remainder of the condensate is transferred and fed to isomerization zone 1 by means of, in order, conduits 18, 20 and 22, isomerization zone feed tank 23, conduit 24, heat exchanger (vaporizer) 25, and conduits 26 and 27. In a second mode of operation, only a portion, e.g. 20 to 80 weight percent, of the vapor effluent from column 14 is condensed in condenser 17 and all of the resulting condensate is returned to column 14 via conduits 18 and 19. The remainder of the vapor effluent from column 14 is transferred and fed to isomerization zone 1 by means of, in order, conduit 16, condenser 17, conduits 21 and 22, isomerization zone feed tank 23, conduit 24, heat exchanger 25, and conduits 26 and 27. The vapor obtained from condenser 17 may be condensed and collected as a liquid in tank 23. This liquid isomerization feed subsequently is vaporized in heat exchanger 25 and fed as a vapor to isomerization zone 1. Carbon monoxide and a nonreactive diluent gas such as nitrogen is added to the isomerization feed through conduit 28.

Isomerization zone 1 comprises one or more reactors, each containing one or more beds of a supported palladium or platinum catalyst. The walls of the isomerization reactors may be insulated or have heat transfer through the walls to a heat transfer fluid.

The process provided by the present invention is further illustrated by the following example using the 2,3-DHF production system described in the FIGURE. The flow rates are given in parts by weight.

A vapor effluent from isomerization zone 1 was condensed and fed to the mid-section of distillation column 4 along with fresh 2,5-DHF. The feed rate to column 4 was 269 parts per hour isomerization zone effluent and 120 parts per hour fresh 2,5-DHF. Distillation column 4 consisted of a 1.8 meter section of 2.54 cm inside diameter, schedule 40 316 stainless steel pipe. The column contained 76.2 cm of 4 mm Penn State packing each in the rectifying and stripping sections of the column, i.e., above and below the feed to the column. A DP cell was used to measure the pressure drop over the column to help set the heat input to reboiler 11 for proper vapor and liquid traffic in the column. Band heaters were used on the rectifying, stripping and feed sections of the column, placed between two layers of insulation. The reboiler consisted of a 30 cm section of 3.8 cm inside diameter pipe heated by a band heater. The power input to the reboiler was set at a constant value and the reboiler level was controlled, by means of a DP cell to measure level, by the bottoms flow rate through a pump. The temperature profile of the column was 53° C. at the top, 57° C. at the mid-point and 64° C. at the base of the column.

A vapor effluent comprising 2,3-DHF was removed from the column at a rate of 1200 parts per hour through conduit 6 and condensed in heat exchanger 7. Approximately 90 weight percent of the condensed effluent was returned to the column via conduits 8 and 9 to control the temperature of the rectifying section. The remainder of the condensed effluent representing the 2,3-DHF product was removed from the production system by means of conduit 10.

Liquid comprising 2,5-DHF was removed from reboiler 11 and fed through conduit 12 to vaporizer 13 at a rate of 270 parts per hour. The vaporizer consisted of a 30.5 cm section of 10.2 cm inside diameter pipe heated by electric band heaters. The liquid level in the vaporizer was maintained using a sight glass. Column 14 consisted of a vacuum-jacketed glass column containing a bed of 4 mm Penn State packing 19 mm in diameter and 35.6 cm in height. Vaporizer 13 produced 389 parts per hour of vapor which entered column 14 which was transported through conduit 16 to condenser 17. 120 Parts per hour of this vapor was condensed in condenser 17 and returned to column 14 as a liquid through conduits 18 and 19. 269 Parts per hour of vapor were transferred through conduits 21 and 22 to tank 23. Alternatively, all of the vapor in conduit 16 could be condensed in condenser 17 and the distillate taken as a liquid through conduit 20.

Liquid feed material comprising 2,5-DHF was removed from tank 23 by means of conduit 24 at a rate of 269 parts per hour, vaporized in heat exchanger 25 and fed via conduits 26 and 27 to isomerization zone 1. Carbon monoxide and nitrogen were supplied by conduit 28 so that the gaseous feed mixture in conduit 27 contained 260 parts per million CO and 5.2 volume percent nitrogen.

The isomerization zone comprised two reactors which contained beds of supported palladium catalysts. The first reactor consisted of a 61 cm section of 1.3 cm inside diameter, schedule 40 pipe with a 3.2 mm thermo-couple down the center. This reactor contained a 28 cm long bed of 1% palladium on silica catalyst (18.7 parts). The second reactor consisted of a 91 cm section of 1.3 cm inside diameter, schedule 40 pipe with a 3.2 mm thermocouple down the center. This second reactor was surrounded by an aluminum block with electric heaters and contained a 59.9 cm long bed of 2% palladium on silica catalyst (37.6 parts). The feed mixture was fed by conduit 27 to the first isomerization reactor and then to the second reactor to provide an isomerization zone effluent to conduit 2. The overall conversion of 2,5-DHF to 2,3-DHF in the isomerization zone averaged 55%.

The 2,3-dihydrofuran production system was operated as described above for four days at near steady-state conditions producing 119 parts per hour of product consisting of over 94% 2,3-DHF. This production rate corresponds to a space-time yield, based on the total volume of catalyst in the two reactors of the isomerization zone of 2.1 parts 2,3-DHF per part catalyst per hour.

The composition of some of the streams of the preceding example are set forth in Table I wherein the values given are weight percentages based on the total weight of the stream compositions. Compositions were determined by gas chromatography.

TABLE I

| Conduit Stream | THF | 2,3-DHF | 2,5-DHF | Furan | EpB | HCr | HBu | MEK |
|---|---|---|---|---|---|---|---|---|
| 2 | 16.00 | 39.89 | 38.26 | 0.60 | — | 0.07 | 3.95 | 0.85 |
| 5 | — | — | 99.32 | 0.08 | 0.07 | 0.36 | — | — |
| 10 | 0.59 | 94.72 | 2.31 | 1.88 | — | — | — | — |
| 12 | 15.33 | 8.89 | 70.93 | — | 0.03 | 0.02 | 3.78 | 0.80 |
| 16 | 15.33 | 8.83 | 70.56 | 0.08 | 0.04 | 0.19 | 3.80 | 0.81 |

Overall mass balance results for the four day period were determined from inputs and outputs relating to the production system. The only input accounted for was the fresh 2,5-DHF feedstock. Outputs were all samples taken and the 2,3-DHF product. Volatile gases such as CO and propylene were not captured. The overall mass balance accounted for 98.8% of the input material. The selectivity to 2,3-DHF was 96.60%.

The invention has been described in detail with particular reference to preferred embodiments thereof, but it will be understood that variations and modifications can be effected within the spirit and scope of the invention.

We claim:

1. Process for the continuous production of 2,3-dihydrofuran (2,3-DHF) by the isomerization of 2,5-dihydrofuran (2,5-DHF) comprising an isomerization zone containing one or more beds of a supported, palladium or platinum catalyst, a product recovery zone comprising a distillation column, a high boiler removal zone and means for feeding 2,5-DHF obtained from the high boiler removal zone to the isomerization zone, comprising the steps of:

(1) feeding the product of step (3) and fresh 2,5-DHF to the distillation column of the product recovery zone to obtain (i) an overhead vapor stream rich in 2,3-DHF from the top or upper section of the column and (ii) a bottoms liquid stream rich in 2,5-DHF from the base or lower section of the column;

(2) feeding liquid from step (1)(ii) to a high boiler removal zone comprising distillation means to obtain (i) a liquid bottoms stream comprising high boilers and (ii) a distillate stream comprising 2,5-DHF; and (3) feeding a vapor comprising 2,5-DHF from step (2)(ii) to the isomerization zone to produce an isomerization product comprising 2,3-DHF and 2,5-DHF.

2. Process according to claim 1 wherein the conversion of the 2,5-DHF fed to the isomerization zone is about 20 to 90 mole percent.

3. Process according to claim 2 wherein a tertiary amine is added to the distillation column or to the high boiler removal zone.

4. Process for the continuous production of 2,3-dihydrofuran (2,3-DHF) by the isomerization of 2,5-dihydrofuran (2,5-DHF) comprising an isomerization zone containing one or more beds of a supported, palladium catalyst, a product recovery zone comprising a distillation column, a high boiler removal zone and means for feeding 2,5-DHF obtained from the high boiler removal zone to the isomerization zone, comprising the steps of:

(1) feeding the product of step (3) and fresh 2,5-DHF to the mid-section of the distillation column of the product recovery zone to obtain (i) an overhead vapor stream comprising, by weight, about 90 to 97% 2,3-DHF, about 0.5 to 5% 2,5-DHF, about 1 to 5% furan, and about 0.1 to 1% tetrahydrofuran from the top or upper section of the column and (ii) a bottoms liquid stream rich in 2,5-DHF from the base or lower section of the column;

(2) feeding liquid from step (1)(ii) to a high boiler removal zone comprising distillation means to obtain (i) a liquid bottoms stream comprising high boiler compounds having a boiling point of above about 120° C. and (ii) a distillate stream comprising, by weight, about 1 to 20% tetrahydrofuran, about 1 to 10% 2,3-DHF, a total of about 1 to 10% of 3,4-epoxy-1-butene, crotonaldehyde, butyraldehyde and methyl ethyl ketone, and about 65 to 95% 2,5-DHF; and (3) feeding a vapor comprising 2,5-DHF from step (2)(ii) to the isomerization zone to produce an isomerization product comprising 2,3-DHF and 2,5-DHF, wherein the conversion of the 2,5-DHF fed to the isomerization zone is about 40 to 60 mole percent.

5. Process according to claim 4 wherein the catalyst is a supported catalyst comprising 0.5 to 3.0 weight percent palladium and the fresh 2,5-DHF fed to the distillation column of the product recovery zone contains about 0.1 to 5 ppm methyl iodide.

6. Process according to claim 5 wherein the feed to the isomerization zone contains about 50 to 750 ppmv carbon monoxide and the isomerization zone is operated at a temperature of about 50° to 130° C.

* * * * *